United States Patent [19]

Beesley

[11] Patent Number: 4,534,644
[45] Date of Patent: Aug. 13, 1985

[54] GUIDES FOR COLOR GRADING FACETED GEMSTONES

[76] Inventor: Casper R. Beesley, 210 Commonwealth Ave., Mt. Vernon, N.Y. 10552

[21] Appl. No.: 477,749

[22] Filed: Mar. 22, 1983

[51] Int. Cl.³ .......................... G01J 3/52; G01N 21/87
[52] U.S. Cl. ....................................... 356/30; 356/421
[58] Field of Search ................. 356/30, 243, 416, 421, 356/422, 423, 424, 425; 350/97, 102; 434/98, 99, 100, 386; 63/26, 32

[56] References Cited

U.S. PATENT DOCUMENTS

| | | | |
|---|---|---|---|
| 1,597,830 | 8/1926 | Rueger | 434/98 |
| 1,612,791 | 1/1927 | Ames et al. | 434/98 |
| 1,617,024 | 2/1927 | Munsell et al. | 434/98 |
| 2,007,264 | 7/1935 | Allen | 434/98 |
| 2,058,073 | 10/1936 | Fritzsching | 356/423 |
| 3,898,869 | 8/1975 | Reneer | 63/26 |

FOREIGN PATENT DOCUMENTS 2036360  6/1980  United Kingdom ................. 356/30

OTHER PUBLICATIONS

"Color Comparators," Magnuson Engineers, Inc.

Primary Examiner—F. L. Evans
Assistant Examiner—Joel L. Harringa
Attorney, Agent, or Firm—Michael Ebert

[57] ABSTRACT

Guides to facilitate color grading of faceted gemstones such as rubies and sapphires. Each guide has a series of simulated standards thereon representing a range of grades for a particular class of colored stones and serving as reference points for comparing an unknown therewith in a standardized lighting environment. The guide is constituted by a strip of reflective metal, foil or metallized film sandwiched between a back panel and a top panel having a row of port holes therein, each exposing a reflective zone on the strip. The zone is embossed to create a radial array of wedge-shaped segments, each of which is serrated to define a series of prism-like steps that run from the apex to the base of the segment to provide a pattern simulating the reflective properties of a step-cut faceted stone. Interposed between each zone and its associated hole is a planar optical filter whose coloration is such that in combination with the underlying reflective zone, it creates a respective color grade in the range thereof. In making a color judgment, the observer seeks the closest match between the unknown being examined and one of the simulated standards on the guide, thereby obviating the need for actual stone standards.

11 Claims, 10 Drawing Figures

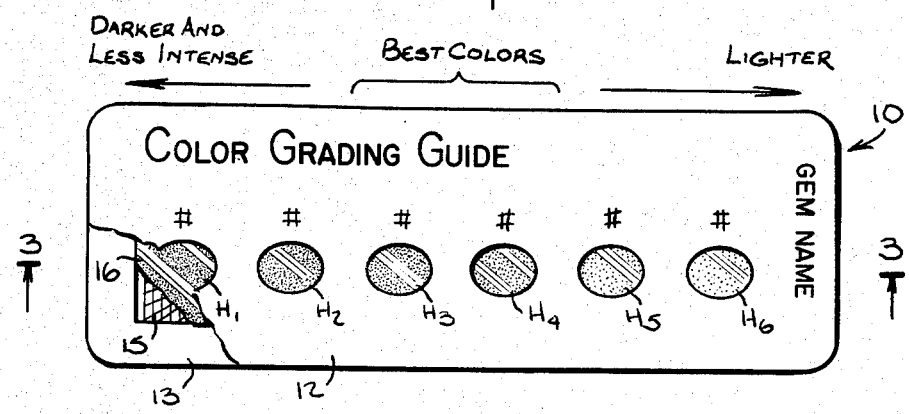
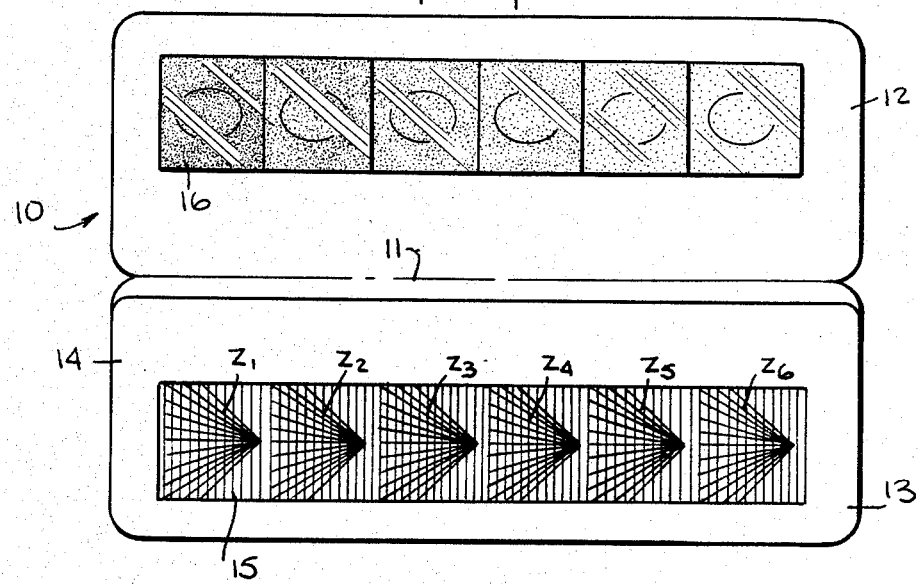
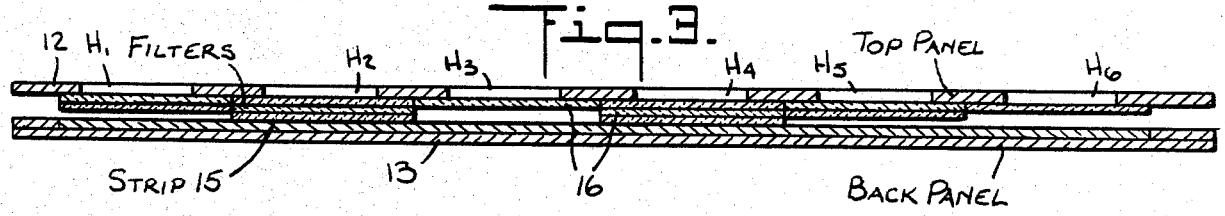

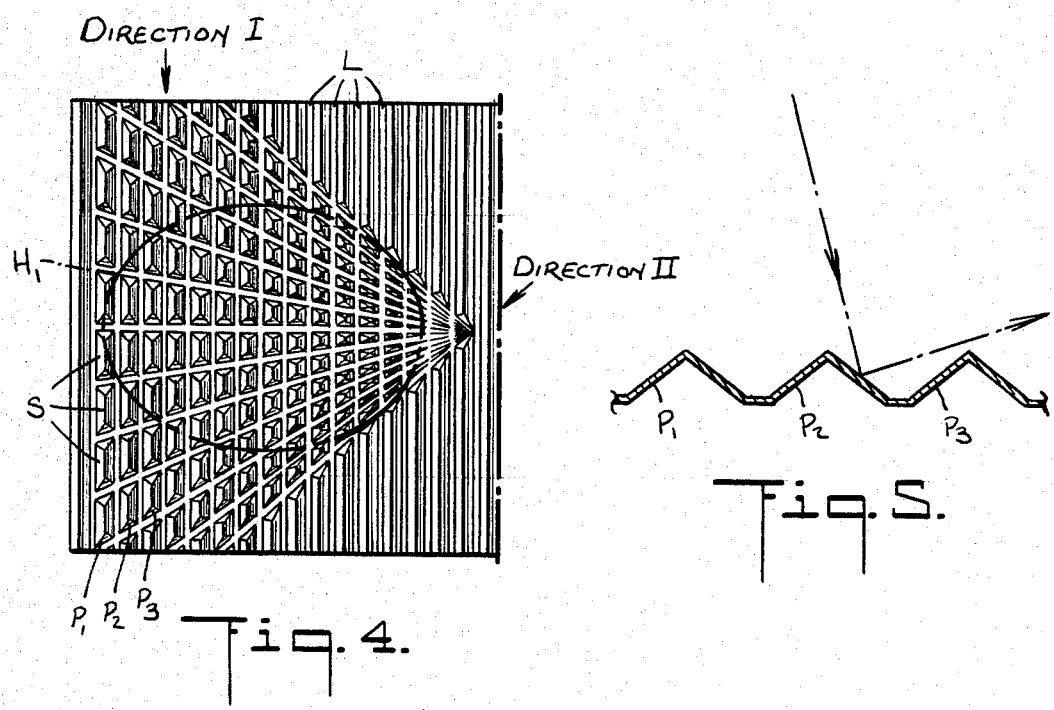
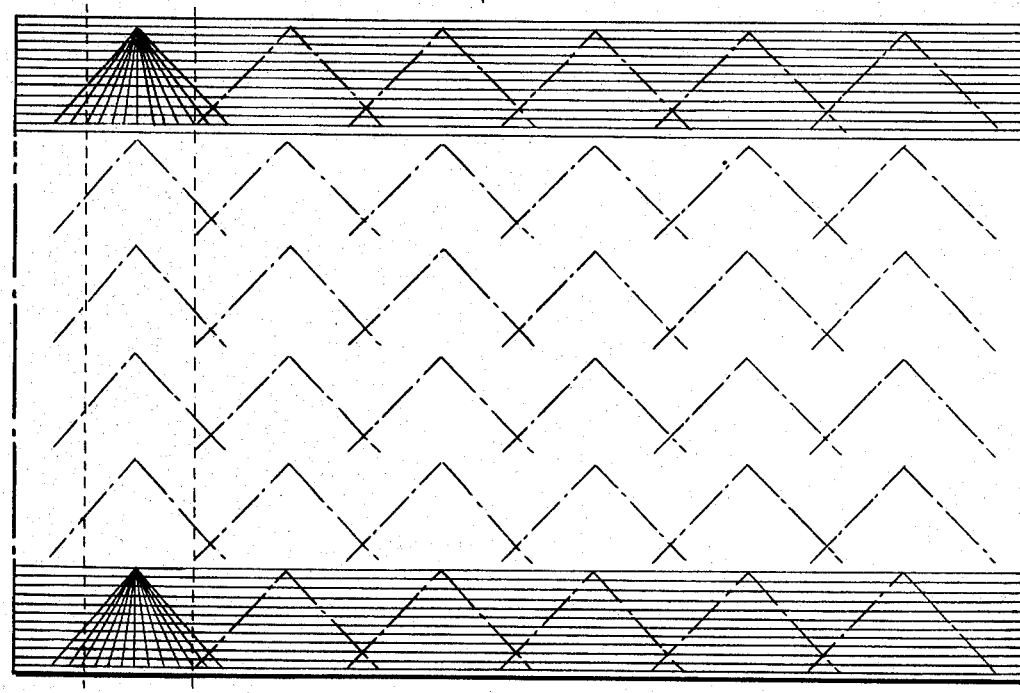

GUIDES FOR COLOR GRADING FACETED GEMSTONES

BACKGROUND OF INVENTION

1. Field of Invention

The invention relates generally to the color grading of gemstones such as rubies, emeralds and sapphires, and in particular to classified color guides for gems, each guide facilitating the color grading of stones falling within a specified class by providing a series of simulated reference standards against which an observer can compare an unknown in that class to determine its color grade.

In establishing the economic value of a precious or semiprecious stone, color represents the most influential factor. Before addressing the problem of color grading gemstones, the essential nature of color must first be examined.

Within the broad spectrum of radiant wave energy lies a narrow band of visible energy which extends through a wavelength range of about 380 to 760 nanometers. Although wavelengths lying above or below this band can affect a gem's appearance, such as those in the infrared or ultraviolet region, they do not directly stimulate the receptors of the eye and are therefore invisible.

A light source emitting radiant energy that is relatively balanced in all visible wavelengths appears to the eye as white. Without light, there can be no color, for color simply represents an imbalance of visible energy reaching the eye from a light source or an object, an imbalance being any deviation from the average amount of all wavelengths in the visible band. All physical objects when exposed to light more or less absorb, transmit or reflect the light impinging thereon and therefore have a modifying effect—reducing both the amount of energy and the nature of the light waves which reach the eye. Thus an object such as a gem affords a particular color impression because it reflects or transmits light waves only in certain narrow ranges, while absorbing all others.

In interpreting the color of an object such as a colored stone, several variables come in play. Not only is color judgment influenced by the nature and intensity of the light source employed, but also by the method of viewing the illuminated object and by its physical configuration and degree of transparency. Moreover, one must take into account the subjective sensitivity of the observer to color.

Thus if one examines a Thai ruby under an incandescent light bulb, the predominance of red wavelengths in this source will accentuate the essential redness of the stone. But when using "daylight" fluorescent illumination to examine the same stone, this will generally cause the stone to assume a purplish-red appearance because of dominant blue wavelengths in this source. On the other hand, under natural daylight illumination of the same ruby, an orange or brownish coloration will often become apparent. In each instance, therefore, the absorption and transmission characteristics of the stone will interact with whatever examination light is available to alter the visible color composition.

A fluorescent "daylight" fixture is a useful illumination source for gem examination; for while this source does not exactly duplicate the unique spectral energy distribution of diffused light reflected from the North Sky, it has the advantage of producing a constant and uniform lighting environment and is therefore an acceptable light source for color grading gems by means of the color guides in accordance with the invention to be described hereinafter.

The color content of a transparent stone may be identified in terms of three basic variables; namely, hue, tone and intensity. Hue is the visible sensation imparted to an observer that permits him to distinguish one color from another. Thus the visual distinctions existing between red, blue, green and other colors represent the hue of a stone. Hue also encompasses color gradations such as orangy-red, yellowish-green and greenish-blue.

Tone is the visual sensation that makes it possible for an observer to recognize shadings in a particular hue on a scale running from light to dark. Thus adding increasing amounts of white to a particular hue, say, pure green, will dilute this color into a range of progressively lighter tints of green. If, however, one adds to pure green increasing amounts of black, this will create progressively darker shades of this color.

Intensity is the visual sensation that reflects the degree of vividness or richness in a color on a scale ranging from vivid to dull. Thus in gem materials, adding brown or gray to a vivid color will reduce its intensity and render it dull to an extent depending on the relative amount of the additive. Conversely, the absence of brown or gray in a gem generally contributes to the vividness of the gem's body color.

When judging the value of a gemstone by grading its color, one is not dealing with a flat, two-dimensional surface, but with a three-dimensional, multi-faceted body cut to a variety of shapes and facet configurations. Color appraisal is further complicated by the presence of pleochroism in many gem bodies. This dichroic or trichroic property describes a mineral's ability to directionally exhibit two or more colors when viewed in various directions or in the same direction. Traditionally, only diamonds, emeralds, rubies and sapphires were considered to be "precious" minerals; all the rest being treated as "semiprecious." However, these terms are currently regarded as meaningless in view of the wide quality variations encountered in any specific gemstone where beauty is the most important desideratum and rarity is also a significant factor.

Transparent gemstones are usually cut into prism-like or faceted configurations to exploit repeated light reflections which create a sparkling, brilliant effect and color amplification typical of fashioned gemstones. Faceted gems are generally cut either in a "brilliant" or a "step-cut" style. The standard brilliant cut is basically composed of numerous triangular facets completely covering the bottom of the stone and partially covering the top thereof in a band directly above the girdle, the major portion of the top being truncated by a single large table facet. The step-cut consists of a series of rectangular or trapezoidally-shaped facets or steps covering the bottom and again partly covering the top. A combination of these two basic cutting styles is commonly used to create various optical effects including scintillation, dispersion and color amplification.

In all faceted gems, light rays enter the top mainly through the table facet, the rays then striking the inclined bottom facets where they are internally reflected upwardly toward the observer's eye. The brilliant cut is largely reserved for diamonds, whereas the step cut or a combination of step and brilliant cuts, is favored for all other gemstones, such as emeralds, rubies and sapphires.

One commonly used technique for grading a colored stone makes use of a set of standards that function as physical reference points for comparing unknowns therewith in a standardized light environment by a trained observer. In the gem industry, these reference standards often take the form of actual stones to which a fixed or general grade has been assigned. Thus for the color-grading of emeralds, one may use a set of, say, ten actual emeralds of progressively better color grade, a match then being sought by the observer between the unknown sample and one of these actual standards.

One disadvantage of using real stones as standards is that they are subject to wear and tear, and may in time require recutting, this giving rise to a change in appearance of the stone. Then, of course, one is faced with the cost of providing a set of actual reference standards for each type of gemstone. The investment entailed thereby may be prohibitive for the typical appraiser.

To overcome this problem, use may be made of glass or plastic imitations which in some cases nearly duplicate the appearance of actual gems. But their color range is limited and difficult to control. This introduces a margin of error in color appraisal which may render it unacceptable for purposes of certification. Moreover, the accurate duplication and reproducibility of actual gem master sets or gem simulants for communication between appraiser and/or dealer in colored stones is a nearly impossible task.

Another approach is to use visual colorimeters in which a reference standard is produced by mixing adjustable amounts of red, green and blue light in order to match the color of an unknown sample. In practice, this leaves much to be desired; for a three-dimensional, multi-faceted gem affords a complex color impression that cannot be accurately simulated by visual colorimetry.

Nor is electronic colorimetry entirely effective in the color grading of gems. In this approach, color filters and sensors are used as an alternative to the eye to electronically monitor the quality and quantity of light emerging from an unknown, the various color components being electronically sensed and measured. But here again, the complicated nature of the gem structure being analyzed creates difficulties in interpretation that render standard measurement techniques of limited value.

One may also analyze the color of a gemstone by spectrophotometry, making use of an instrument which breaks light into its component wavelengths, each slice in the spectrum passing through the sample being tested, and being then converted into a corresponding digital value which is analyzed in a computer. Though this approach is at least theoretically capable of affording a precise analysis of the color characteristics of a gem stone, the cost of this instrument and the operating skills entailed thereby are beyond the means and capabilities of the average stone appraiser.

SUMMARY OF INVENTION

In view of the foregoing, the main object of this invention is to provide a set of guides to facilitate the color grading of faceted gemstones such as rubies, emeralds and sapphires.

More particularly, an object of this invention is to provide color grading guides each having a series of simulated standards thereon representing a range of grades for a particular class of colored stones and serving as reference points for comparing an unknown therewith under standardized lighting conditions in order to assign a quality grade to the unknown.

A significant advantage of a color grading guide in accordance with the invention is that the simulated standards have three-dimensional optical properties analogous to those of actual stone standards, which properties are reproducible and not subject to the same level of wear and tear as real stone standards. Moreover, the cost of a guide consisting of a series of simulated standards is insignificant as compared to a corresponding series of actual standards; hence an appraiser may be supplied at relatively low cost with a set of reproducible guides covering virtually all colored stones and thereby be relieved of the need and expense to acquire actual standards.

Also an object of this invention is to provide a color grading guide whose structure is essentially the same for all colored stones, the difference between one guide and another lying in the nature of the optical filters incorporated therein.

Yet another object of the invention is to provide guides for facilitating the color grading of faceted gem stones which may be efficiently mass-produced and thereby made widely available to the industry, the guides being simple to use, yet affording accurate color grading.

Briefly stated, these objects are attained in guides to facilitate color grading of faceted gemstones such as rubies and sapphires. Each guide has a series of simulated standards thereon representing a range of grades of a particular class of colored stones and serving as reference points for comparing an unknown therewith in a standardized lighting environment. The guide is constituted by a strip of reflective metallized film or metal foil sandwiched between a backing panel and a top panel having a row of port holes therein each exposing an oval zone on the strip. The zone is embossed to create a radial array of wedge-shaped segments, each of which is serrated to define a series of prism-like steps that run from the apex to the base of the segment to provide a pattern simulating the reflective properties of a step-cut faceted stone.

Interposed between each zone and its associated hole is a planar optical filter whose coloration is such that in combination with the underlying reflective zone, it creates a respective color grade in the range thereof. This combination of elements forms a standard that simulates the appearance of an actual gemstone having a given grade and closely duplicates the passage of light in the gem material without possessing the three dimensionality of the actual stone. In a gemstone as well as in the color comparison, standard light passes through a colored medium and is reflected back from a reflective surface and amplified as it passes back through the colored medium to emerge therefrom toward the eye of the observer.

OUTLINE OF DRAWINGS

For a better understanding of the invention as well as other objects and further features thereof, reference is made to the following detailed description to be read in conjunction with the accompanying drawings, wherein:

FIG. 1 illustrates a color-grading guide in accordance with the invention, partly cut away;

FIG. 2 shows the card from which the guide is made in the unfolded state to expose the elements of the guide;

FIG. 3 is a longitudinal section taken through the guide shown in FIG. 1, in the plane indicated by line 3—3.

FIG. 4 is an enlargement of one reflecting zone in the guide to show the embossing pattern thereof;

Figure 7:
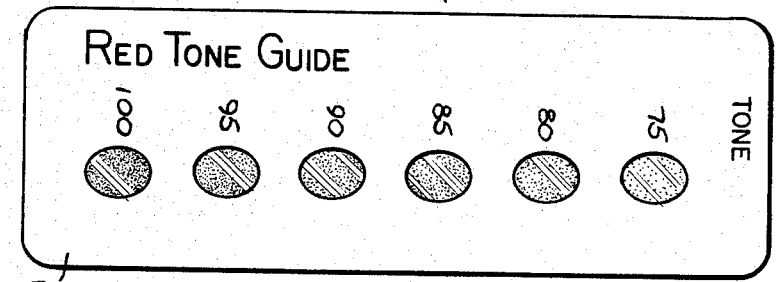
Figure 8:
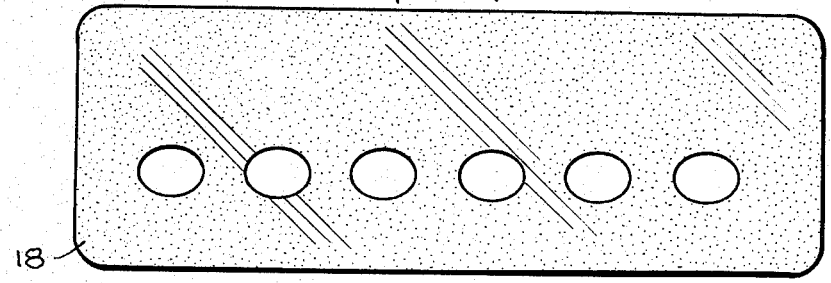
Figure 9:
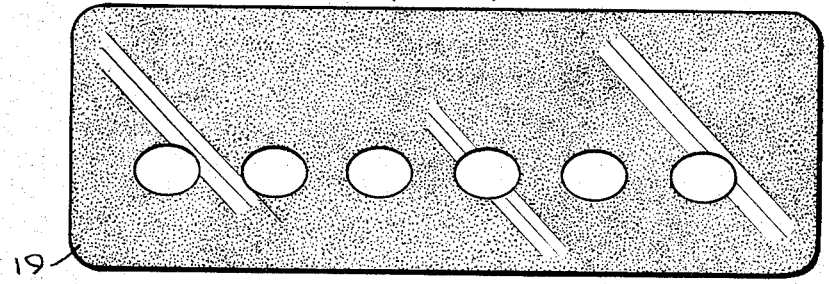
Figure 10:
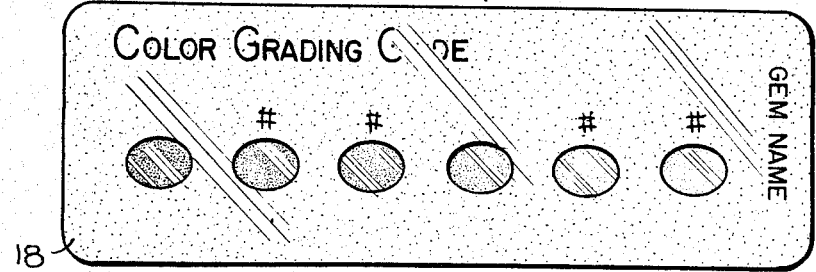

FIG. 5 schematically illustrates the relationship of incident light to the embossed surface of the zone;

FIG. 6 shows the multiple pattern in the die for producing the zones;

FIG. 7 illustrates a tone guide in accordance with the invention;

FIG. 8 shows one sample of an intensity-control mask to be used in conjunction with a color-grading guide;

FIG. 9 showns another sample of an intensity-control mask;

FIG. 10 shows an intensity-control mask superposed in a color-grading guide.

DESCRIPTION OF INVENTION

Referring now to FIGS. 1 and 2, there is shown a color-grading guide for faceted gemstones in accordance with the invention, the guide including a rectangular card 10 which is provided with a fold line 11 to define a top panel 12 and a rear panel 13. In practice, the card may be made of cardboard or synthetic material.

Punched into top panel 12 and extending thereacross is a row of six oval port holes $H_1$ to $H_6$ having three digit grade numbers 233 to 238 assigned thereto representing a scale of different color grade values. The guide shown, by way of example, is for the color grading of garnet stones. In practice, a separate guide or series of guides is provided for each class or type of faceted gem stones; i.e., ruby, emerald, aquamarine, sapphire, tourmaline, spinel and so on, so that the user then has available a color-grading guide for whatever unknown he is called upon to appraise.

The number of guides for each species of stone is determined by the range of standards needed to adequately cover the gem type under examination. The greater the value difference between two colors, the more the need for standards to fully encompass the gem range being examined.

Applied to back panel 13 within a mat 14 bonded thereto is a strip 15 formed of silver or aluminum foil or metallized polyester film having specular properties. Embossed on the strip is a series of six square zones $Z_1$ to $Z_6$, which register with the correspondingly numbered holes $H_1$ to $H_6$. These holes have an oval shape to simulate the usual shape of a typical gemstone. In practice, other hole shapes may be used to simulate special stone shapes.

The embossing pattern, in each zone as shown separately in FIG. 4 is such as to create a radial array of wedge-shaped segments S, each of which is serrated by parallel score lines L to form a chain of prism-like steps $P_1$, $P_2$, $P_3$, etc. of increasingly greater width, running from the apex of the wedge-shaped segment to the base thereof.

The pattern impressed on the reflecting zone simulates the reflective characteristics of a transparent, step-cut faceted stone with respect to light rays directed toward the table of the stone and gives rise to comparable multiple reflections. In practice, the embossing pattern in multiple form may be engraved in a hard metal die and impressed on a foil sheet in a press, the sheet therewith being cut into individual strips. This multiple pattern form is shown in FIG. 6.

One of the more important factors in color judgment is the quality and appearance of colored light that emanates from the gem's pavillion surfaces or facets. The standard procedure in examining the color of a gemstone is to so position it that the observer can then view the light emerging from those areas of the gem where the greatest amount of light is returned to the eye. In the overwhelming majority of cases, the areas which achieve this objective on standard oval or cushion antique shapes are found on the narrow ends of both cutting styles. The embossing pattern selected as a standard format for the color-grading guide closely resembles the specific area of the stone which is representative of the most common area for examining body color in a gem.

Since the upper surface of the reflective pattern in the zone functions in much the same manner as the table and pavillion facets of a gem, the indentation angle in directions I in FIG. 4, which is the direction of the transverse serrations across strip 15, is formed to afford a high level of reflectivity to the eye while minimizing glare from the upper surface of the pattern. The indentation angle in radial directions II is relatively shallow, for its primary function is to provide dark areas that break up the light to simulate the optical properties of a multi-faceted gem.

It will be noted in FIG. 4, which outlines the relationship of a port hole $H_1$ with respect to the embossing pattern, that the pattern is placed off center so that the observer will not be distracted by the appearance of 100% brilliancy which rarely occurs in a gem; that is, a gem that uniformly reflects light from the girdle edge to the culet on a level line. Also, the angular relationship simulating the facet pattern used in the color-grading guide is arranged to allow analysis by colorimeter or spectrophotometer for quality control purposes.

Covering the underside of each port hole is one or more slides 16 of optical film material which is tinted to act as a selective absorption filter; that is, a filter which transmits certain wavelengths more than others. Thus, assuming a green hued filter slide, this tends to absorb the red and blue portions of the spectrum while passing the green portion. A red-hued slide will pass the red portion of the visible light spectrum and more or less absorb other portions. The term planar optical filter as used herein designates a single slide or a stack of slides which together produce the desired hue. Thus subtle variations in color appearance may be produced by changing the number of slides in stack thereof, each slide introducing a slight change in color. This degree of fine control is essential for in certain gems a minor variation in color can result in a major variation in value.

Thus for sapphire grading, all of the optical filters in the six port holes will be blue, but in shadings appropriate to the grade. For a light blue, one may use a single, lightly-tinted blue slide 16; for a somewhat darker blue, two such lightly-tinted slides may be used in combination; for an even darker blue, one may combine a lightly-tinted slide with a darker blue slide; and for an even deeper blue, two dark blue slides may be combined, thereby establishing a standard appropriate to each grade.

In examining an unknown gem, the primary concern is not how its color was spectrally formed or the absorption pattern of the mineral that gives rise to the total visual effect, but to identify the visual consequences of white light interacting with a colored, three-dimensional solid. The final result is a combination of primary and secondary colors and intensity modifiers. Thus while a typical ruby is primarily red in color, a color scan thereof will indicate in a given sample that the ruby color is 70% red, 20% orange and 10% purple/pink. Hence for purposes of rating a ruby on a color scale representing its purity, the highest rating would be assigned to a ruby having the maximum percentage of red, and the lowest to a ruby having the minimum percentage of red.

In the color-grading guide shown in FIG. 1, which has a row of six standards, the basic arrangement is such that the best colors are represented by the two center port holes H₃ and H₄. The port holes H₅ and H₆ to the right thereof represent progressively lighter standards and the port holes H₂ and H₁ to the left thereof represent darker and less intense standards. The colors on each card are arranged to provide some degree of contrast in color from the standpoint of hue, tone and intensity.

The color grading guide utilizes the eye to make a comparison between the unknown gem in the class for which the card is designed (Garnet in the case of FIG. 1) and the series of standards on the card. It is a well established fact that the eye's ability to judge color difference under controlled conditions is excellent when a range of colors is provided as reference points or standards.

The three digit numbers 233 to 238 which appear in the Garnet guide card are code numbers for Garnet which can be decoded in a guide book or card file for use in comparison with the cards. In the book or file, each listed code number is followed by a text appropriate to the grade represented by the code number. This text may include (a) American Gemological Laboratories (AGL) grading information such as 4.5/80, (b) a National Bureau of Standards—Universal Color Language description (c) C.I.E. or modified C.I.E. Mathematical color descriptions and (d) a gem description, including country of origin or geographic information, when relevant. Thus many of the colors generated in the color grading guides are indicative of a particular country or origin. For example, in a color-grading guide for sapphire, a port hole number 350 (or whatever other number is assigned), provides a standard whose color appearance is that of a Kashmir Sapphire, not just a sapphire. And in a guide for emeralds, port holes having code numbers 185 to 190 cover the color range normally associated with Columbian Emeralds; whereas port hole code numbers in a range of No. 191 to 196 encompass the African Emerald color range. In a Peridot guide, port hole code number 275 is typically associated with Peridots from Norway. This geographical information which is important in gem appraisal is given in the text associated with the code numbers.

The thickness of the optical filter slides is exaggerated for purposes of illustration. In practice, each slide has a thickness of a few mils; and while one stack may have a total thickness greater than another stack or a single strip; the top panel 11, which is preferably of paper card stock and therefore flexible, abuts all of the filters in the row and there is no separation therebetween, even though FIG. 3 shows a separation in some cases.

In optical terms, the white light entering each port hole passes through the optical filter and strikes the embossed reflecting zone surface of the foil which simulates a step-cut gem and acts to produce multiple reflections, the reflected rays passing through the filter on its way toward the eye of the observer to generate the visual effect of a faceted gem of the grade in question.

The observer, who also has the unknown gem before him in the same light environment places the gem on the guide and then compares the visual effect produced thereby with each of the simulated standards on the guide in search of that standard which most closely matches the visual effect of the unknown. The reason the port holes on the guide are displaced from the center line is to allow room for the unknown gem which is then observed on the same background. In practice, the panel is white, which is the common background for the gem and the standards.

The colors on each guide provide a large measure of contrast in color from the standpoint of hue, tone and intensity. However, in some instances, the appraiser may not be able to find a close match between the unknown gem and the series of standards on the guide with respect to the tone and intensity factors.

As explained previously, tone represents the quantity of a given hue on a scale running from light to dark. In order to make a more exact determination of tone independent of hue and intensity, tone guides are provided, such as the guide 17 shown in FIG. 7. This has six port holes as in the case of the color-grading guides, and an embossed reflecting zone associated with each hole. However, in this instance, the optical filters afford progressive step gradations in one color, a separate set of tone guides being provided for red, green and blue, the colors which cover most gems.

Assuming a red tone guide, the first port will have a faintly tinted red slide, the second a lightly tinted red slide, the third a less lightly tinted slide, and so on. To adequately cover the full scale of tone values, three tone guides may be used, each having six tone steps. Thus the tone grades on the first card may be in color tone steps of 5—10—20—30—40—50; the second in color tone steps of 50—55—60—65—70—75; and the third, which is the tone guide illustrated, in color tone steps of 75—80—85—90—95—100.

In practice, therefore, say, with an unknown red ruby whose tone is to be more exactly defined, one then seeks a match between the unknown, and a tone standard on the tone guides for this color.

Intensity, as explained previously, is the degree of vividness or richness in a color on a scale from vivid to dull. The intensity of a gem as perceived by the eye depends not only on the amount of light impinging thereon but also on the background against which the gem is observed. The iris, which is the pigmented area of the eye, has a perforated center and appears as the pupil. The pupil dilates and contracts by muscular action to regulate the amount of light entering the eye. Thus in order to see in a dimly lit room, the pupil dilates to exploit the available light, while in a very brightly lit room, the pupil contracts to limit the light input to the eye.

The degree of dilation or contraction of the pupil is determined by the overall environmental light, not by the light emanating from the particular object being observed. Thus the illuminated image on a small TV screen appears to have much greater intensity in a darkened room than the same image when the room is brightly lit, for the image is seen through a dilated pupil. By the same token, a gem, as seen against a standard, both of which appear on a white card serving as a background, has a lesser apparent intensity than when the background is dark.

In order to effect matching as to intensity, overlay masks, such as masks 18 and 19 shown in FIGS. 8 and 9, are provided. These masks have the same rectangular dimensions as the color-grading guides and are formed of film material in different shades of gray, from light gray to black. Thus mask 19 is dark relative to mask 18. The masks are provided with port holes corresponding to the holes on the guides, so that by superposing a mask on a guide, as shown in FIG. 10, one can then switch the background from white to the selected shade of gray and thereby alter the apparent intensity of the standards and the unknown stone to be compared therewith to facilitate a proper intensity match.

Special effect guides may also be produced which simulate the dichroic effect characteristic of gems. In this instance, instead of optical filter slides having a uniform color, using photographic techniques, slides may be produced in which the resultant slide has shadow areas thereon. One can also by photographic techniques produce slides which simulate color zoning and texture, these being elements which influence the quality of some gems. It is to be noted in this regard that dichroic effects are more detrimental to sapphires and rubies than to emeralds.

Thus a color grading guide set in accordance with the invention provides a simple and rapid technique for color grading gemstones that is consistent and accurate, yet is relatively inexpensive as compared to techniques heretofore known.

While there has been shown and described a preferred embodiment of guides for color grading faceted gemstones in accordance with the invention, it will be appreciated that many changes and modifications may be made therein without, however, departing from the essential spirit thereof. Thus instead of creating optical filters in progressively different shades of a given hue, by stacking film slides in the manner illustrated, a single slide may be used for each filter having a tone appropriate to its grade number.

I claim:

1. A set of guides for facilitating the color grading of faceted gemstones of different types, each guide being adapted to grade stones of a particular type under standardized conditions of illumination and comprising:
(A) a back panel having a front panel thereover provided with a longitudinal row of port holes;
(B) a reflective strip sandwiched between said panels and having in the zones under said holes an embossed pattern creating multiple reflections; and
(C) a planar optical filter interposed between each hole and its associated zone to interact with the light reflected thereby to simulate the visual impression of a standard grade of said stone of a particular type, the respective filters for the row of holes being such as to provide a range of standard color grades, whereby in making a color judgment, the observer seeks the closest match between the unknown under examination and one of the guide standards.

2. A guide as set forth in claim 1, wherein said holes have an oval shape.

3. A guide as set forth in claim 1, wherein said panels are constituted by a rectangular card which is folded in half to define said back and front panels.

4. A guide as set forth in claim 3, wherein said front panel has a center line and said row of holes is offset with respect to the center line on said front panel to provide a space to place said unknown.

5. A guide as set forth in claim 1, wherein at least six holes are provided in the row thereof.

6. A guide as set forth in claim 1, wherein said strip is formed of a metallized polyester having good spectral properties.

7. A guide as set forth in claim 1, wherein said strip is formed of aluminum foil.

8. A guide as set forth in claim 1, wherein said optical filter is constituted by one or more slides of tinted film material.

9. A guide as set forth in claim 1, wherein said pattern is constituted by a radial array of wedge-shaped segments, each serrated to create a series of prism-like steps running from the apex of the segment to the base thereof to simulate a step-cut faceted gem.

10. A guide as set forth in claim 1 operating in conjunction with at least one overlay mask having corresponding holes and formed of tinted film material in a predetermined shade of gray to modify the apparent intensity of the guide standards.

11. A guide as set forth in claim 1 operating in conjunction with a tone guide having the same structure as the color grading guide but making use of respective optical filters having a common color and a different degree of tone, whereby each port hole affords a different level in tone.

* * * * *